United States Patent [19]

Shroot et al.

[11] Patent Number: 4,961,922

[45] Date of Patent: Oct. 9, 1990

[54] COMPLEXES BASED ON ANTHRALIN AND A STEROL, A PROCESS FOR OBTAINING THEM AND THEIR USE IN THERAPEUTICS AND COSMETICS

[75] Inventors: Braham Shroot, Antibes; Daniéle Caron; Jean-Claude Caron, both of Valbonne; Alain Brzokewicz, Antibes, all of France

[73] Assignee: Centre International De Recherches Dermatolociques, Valbonne, France

[21] Appl. No.: 337,800

[22] Filed: Apr. 13, 1989

[30] Foreign Application Priority Data

Apr. 14, 1988 [LU] Luxembourg .......................... 87 201

[51] Int. Cl.⁵ .......................... A61K 7/06; A61K 7/075
[52] U.S. Cl. .......................... 424/70; 424/47; 514/732; 514/861; 514/863; 514/880
[58] Field of Search .................... 424/47, 70; 514/732, 514/863, 861, 880, 886, 922; 260/397.2

[56] References Cited

U.S. PATENT DOCUMENTS 4,513,011 4/1985 Grollier et al. ...................... 514/863
4,743,597 5/1988 Javitt et al. .......................... 514/863

FOREIGN PATENT DOCUMENTS 2107589 5/1983 United Kingdom .
2143433 2/1985 United Kingdom ................ 514/863
2164254 3/1986 United Kingdom ................ 514/732

*Primary Examiner*—Thurman K. Page
*Assistant Examiner*—Amy Hulina
*Attorney, Agent, or Firm*—Wegner & Bretschneider

[57] ABSTRACT

A complex based on anthralin and a sterol, characterized in that its melting point is 10 to 25 degrees Celsius lower than that of the constituent of the complex melting at the lowest temperature and that the proportion of anthralin varies between 10 and 90 mol %.

14 Claims, No Drawings

COMPLEXES BASED ON ANTHRALIN AND A STEROL, A PROCESS FOR OBTAINING THEM AND THEIR USE IN THERAPEUTICS AND COSMETICS

The object of the present invention is complexes based on anthralin and a sterol, a process for obtaining them and their use in therapeutics and cosmetics. The main indications relate to the treatment of inflammatory conditions of the skin, nails and scalp, especially the treatment of psoriasis, eczema and warts.

Among the substances that are particularly active in the treatment of psoriasis, anthralin or dithranol, despite their disadvantages remain the treatment of choice.

The main disadvantages of anthralin are essentially its lack of stability, which causes the formation of brownish spots on the skin and clothing, and its ability to irritate the skin.

In fact, anthralin is particularly unstable, and it undergoes degradation by autoxidation to form the dimer of anthralin (or 1,8,1', 8'-tetrahydroxy-10,10'-dianthrone) and by oxidation to form other degradation products, including 1,8-dihydroxy-9,10-anthraquinone.

Certain degradation products are inactive in the chemotherapy of psoriasis and are mainly responsible for the irritations and the spots on the skin and clothing.

Numerous studies have been undertaken with a view to improving the stability of anthralin, and they have led to diverse suggestions.

Among those suggestions, it is possible in particular to cite the use of stabilizing agents such as those described in U.S. Pat. Nos. 4,287,214 and 4,367,224, or the use of certain vehicles, particularly fatty acid esters such as those described in U.S. Pat. No. 4,316,902 and French Patent Nos. 81.19952, 82.01327 and 84.13431.

These diverse solutions have, however, proved during use to be not entirely satisfactory, since the stabilizing agents do not permit prolonged storage and the new vehicles do not favor good penetration of the anthralin through the skin.

The foregoing indicates that if the stability of the anthralin can be influenced satisfactorily, it ought to be possible simultaneously to solve the problems due to the irritation of the skin and the formation of spots on the skin and on clothing.

After numerous studies, it has now been found that the searched-for stabilization of anthralin could be obtained by forming complexes with certain sterols.

It has been shown in fact that anthralin, by virtue of its chemical structure, has intramolecular hydrogen bonds between the 1,8-hydroxyl groups and the carbonyl group in the 9-position.

These hydrogen bonds act as stabilizers of this molecule. In fact, if they are suppressed, for example in a polar solvent, activation of the $C_{10}$ position occurs, leading to rapid decomposition of the molecule.

The maintenance of hydrogen bonds would therefore be one means for improving the stability of anthralin. This was achieved according to the present invention by the creation of electrostatic interactions in the anthralin-sterol complexes. The examination of spectra obtained by reflection in the near infrared seems to confirm the existence of these interactions.

In fact, it has been proved that the complexes according to the invention had excellent stability in time, even when the support was not anhydrous and, moreover, that the pharmacological properties of the anthralin were retained and even reinforced.

As regards the activity of the complexes according to the invention, it is also possible that the sterol potentiates the effects of the anthralin and acts on the inflammations of the skin.

The object of the present invention is therefore, as a new industrial product, a complex based on anthralin and a sterol, the complex having a melting point 10° to 25° C. lower than that of the constituent of the complex melting at the lowest temperature, the proportion of anthralin varying between 10 and 90 mol %.

The sterol is preferably selected from among:
cholesterol,
the derivatives that contain mono- and polyhydroxy or carboxy substituents on the $C_{17}$ side chain of cholesterol and the lower alkyl $C_1$-$C_6$ esters of said derivatives, and particularly 25-hydroxycholesterol, 20-hydroxycholesterol and the methyl ester of (3-hydroxychol-5-en)-24-oic acid,
the derivatives obtained by isomerization and/or creation of unsaturated bonds in the $C_{17}$ side chain of cholesterol, and particularly stigmasterol, and
the esters with up to 12 carbon atoms and ethers with up to 6 carbon atoms in the $C_3$ position of cholesterol, and particularly cholesterol acetate.

As indicated above, the proportions of anthralin in the complex can vary, depending on the cholesterol derivative, between 10 and 90 mol %, these proportions nevertheless being capable of small variations on the order of ±0.05 mol % for each of the complexes.

Among the different particularly preferred complexes according to the invention, the following can be listed in appropriate molar ratios:

(i) anthralin (0.26 mol %) - cholesterol (0.74 mol %)
(ii) anthralin (0.70 mol %) - 25-hydroxycholesterol (0.30 mol %)
(iii) anthralin (0.30 mol %) - stigmasterol (0.70 mol %)
(iv) anthralin (0.42 mol %) - cholesterol acetate (0.58 mol %)
(v) anthralin (0.17 mol %) - 20-hydroxycholesterol (0.83 mol %)
(vi) anthralin (0.35 mol %) - methyl ester of (3-hydroxychol-5-en)-24-oic acid (0.65 mol %)

The determination of the molar proportions for each of the complexes was performed by differential thermal analysis on the basis of the determination of a binary phase diagram.

The exact proportions of each of the constituents is determined by extrapolation, the complex thus defined having the appearance of a pure product during the determination of its purity by differential thermal analysis.

The different complexes according to the invention exist in the form of a more or less strongly yellow-colored powder, and they are characterized by their melting point, which is 10° to 25° C. lower than that of the constituent melting at the lowest temperature.

For example, the melting points of the complexes cited above are the following:
anthralin - cholesterol: 132°±2° C.,
anthralin - 25-hydroxycholesterol: 157°±2° C.
anthralin - stigmasterol: 150°±2° C.
anthralin - cholesterol acetate: 102°±2° C.
anthralin - 20-hydroxycholesterol: 118°±2° C.
anthralin - methyl ester of (3-hydroxychol-5-en)-24-oic acid: 126°±2° C.

The melting points of the anthralin and of the sterols of these complexes are the following:
anthralin: 176°–180° C.
cholesterol: 148°–149° C.
25-hydroxycholesterol: 178°–180° C.
stigmasterol: 170° C.
cholesterol acetate: 115°–116° C.
20-hydroxycholesterol: 128°–129° C.
methyl ester of (3-hydroxychol-5-en)-24-oic acid: 143°–144° C.

The analysis of the complexes according to the invention by near infrared reflection on an InfraALYZER instrument of the TECHNICON corporation has made it possible to distinguish the complexes according to the invention from the different corresponding physical mixtures without ambiguity.

According to this method of analysis, a sample placed in a specific measuring cell is subjected by means of an appropriate optical system to infrared radiation of wavelengths that, depending on the instrument, are varied between 700 and 2600 nm (InfraALYZER model 450, 19 wavelengths selected by filters) and between 700 and 3800 nm (InfraALYZER model 500, monochromator using the entire spectral range). The light reflected by this sample is concentrated by a photometric integrator and analyzed by an appropriate photodetector:

To each emitted wavelength there is associated a value of absorbance by the sample. The statistical treatment of these results makes it possible to perform qualitative and quantitative determinations of the complexes in question both in the pure state and in a formulation.

Anthralin, the sterol in question and their physical mixture in the molar proportions of the complex are used as reference products for each identification of a complex.

Another object of the present invention is the process for preparation of complexes of the type defined above.

This process consists in heating, under agitation and under nitrogen, a mixture of anthralin and of the sterol in the molar proportions mentioned above and determined by differential thermal analysis, at a temperature close to that of the melting point of the compound that has the highest melting temperature, generally 5° to 10° C. higher, in maintaining this temperature for a time of between approximately 10 and 20 minutes and in allowing the mixture to cool slowly to room temperature. The solid product obtained is then crushed in the form of a powder.

Another object of the present invention is a pharmaceutical or cosmetic product intended for the treatment of the skin, the nails or the scalp, this composition containing, as active substance, at least one anthralinsterol complex of the type defined above in a proportion of between 0.5 and 10% by weight, in a pharmaceutically or cosmetically acceptable vehicle.

The compositions according to the invention are preferably vaseline-based ointments or emulsions of the water-in-oil type, or they can also exist either in the form of a film in which the insoluble complex is dispersed or even in dry form.

The emulsions can contain, as thickening agent, an elastomeric silicone of the polyvinyl dimethylsiloxane type associated with a silica bulking agent.

The elastomeric silicones can be represented by the following formula:

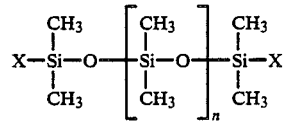

in which:

X represents OH and n is such that the viscosity of the elastomeric silicone associated with the silica bulking agent is between approximately 650 and 1150 cps measured at 24° C.

Such products are described in particular in French Patent No. BSM 8424M.

As a preferred elastomeric silicone, it is possible in particular to mention the product sold by the DOW CORNING CORPORATION under the name of "DOW CORNING MDX-4-4210", that is presented in the form of a kit consisting on the one hand of a base product (elastomeric silicone+silica) and on the other hand of a cross-linking agent or vulcanization catalyst, the base product being used alone to form the thickening agent or also being doped with its cross-linking agent if it is desired to obtain a formulation in the form of a film.

These compositions can also contain an antioxidizing agent of the salicylic acid or butylhydroxytoluene type in a proportion of less than 0.5%.

In a clinical study for evaluation of the anthralin-cholesterol complex in the treatment of psoriasis, ointments containing 1.7 and 5.7% of this complex were compared with hospital preparations of anthralin having equivalent concentrations.

Under the conditions of the study, the formulations containing the anthralin-cholesterol complex are effective and perfectly tolerated by the patients. The mean time necessary to obtain whitening of the skin is 19.3 days for the complexes and 27.1 days for the hospital preparations. The tolerance of the formulations containing the anthralin-cholesterol complex is better than that of the hospital preparations, and appears to be remarkable (absence of sensations of burning skin, reduced cutaneous pigmentation and absence of spots on the skin and clothing).

Examples of preparation of the complexes according to the invention as well as examples of pharmaceutical and cosmetic compositions will now be given, said examples being illustrative and in no way limitative.

PREPARATION OF THE COMPLEXES

Preparation of the anthralin (0.26 mol %) - cholesterol (0.74 mol %) complex

Into a round-bottomed flask equipped with a stirrer and a nitrogen inlet there are introduced 10 g (0.044 mole) of anthralin and 48.83 g (0.126 mole) of cholesterol in powdered form. The mixture is heated slowly to 190° C. and maintained at that temperature for 15 min. The mixture is allowed to cool slowly to room temperature, the stirring and the stream of nitrogen being maintained. After crushing, the target complex has the form of a yellow powder having a melting point of 132°±2° C.

By means of the same procedure as that described above, the following complexes were prepared:
(a) anthralin (0.42 mol %) - cholesterol acetate (0.58 mol %)
melting point=102°±2° C., (b) anthralin (0.30 mol %) - stigmasterol (0.70 mol %) melting point=150°±2° C., (c) anthralin (0.70 mol %) - 25-hydroxycholesterol (0.30 mol %) melting point=157°±2° C., (d) anthralin (0.17 mol %) - 20-hydroxycholesterol (0.83 mol %) melting point=118°±2° C., (e) anthralin (0.35 mol %) - methyl ester of (3-hydroxychol-5-en)-24-oic acid 0.65 mol %) melting point=126°±2° C.

EXAMPLE 1

OINTMENT

| Anthralin - cholesterol complex | 5.68 g |
|---|---|
| Vaseline | 94.32 g |

This ointment is prepared in the cold by mixing 5.68 g of the anthralin-cholesterol complex and 94.32 g of white vaseline. After mixing and homogenization in the three-cylinder mill, the ointment is then packaged in a tube or can.

No degradation of the composition was observed after storage for 12 months at 37° C.

EXAMPLE 2

WATER-IN-OIL EMULSION

| "Dow Corning MDX-4-4210" elastomeric silicone | 38.51 g |
|---|---|
| "DOW CORNING Q2-3225C" self-emulsifying volatile silicone | 39.29 g |
| Thick paraffin oil | 0.78 g |
| Anthralin - cholesterol complex | 5.68 g |
| Distilled water | 15.74 g |

After the elastomeric silicone has been mixed with the volatile silicone, the distilled water is added slowly under stirring in such a manner so as to obtain a homogeneous emulsion.

The anthralin-cholesterol complex is then dispersed slowly in the obtained emulsion.

This emulsion remains stable during storage at room temperature for a time period of longer than 12 months.

EXAMPLE 3

FILM

| Anthralin-25-hydroxy cholesterol | 5.68 g |
|---|---|
| "Dow Corning MDX-4-4210" elastomeric silicone | 85 g |
| "Dow Corning MDX-4-4210 curing agent" vulcanization agent | 9.32 g |

This film is obtained according to the following process:

The base silicone and its vulcanization agent are mixed in a mortar and then the anthralin-cholesterol complex is dispersed slowly while mixing by means of a spatula.

After homogenization in the three-cylinder mill, approximately 500 mg of the preparation obtained in this way is cast on a glass plate. This preparation is degassed with a diaphragm vacuum pump and the degassing is completed with a vane pump.

When the preparation no longer exhibits air bubbles, a second glass plate is applied progressively on the first plate and the two plates are pressed together by means of an appropriate clamping system.

The assembly is then placed in an oven at 75° C. for 45 minutes, and thereafter it is allowed to cool and the film is peeled off.

EXAMPLE 4

DRY FORM

A dry form can be obtained by mixing the following compounds:

| Anthralin - cholesterol complex | 5.68 g |
|---|---|
| Zinc peroxide | 5 g |
| Precipitated pure silica | qsp 100 g |

EXAMPLE 5

POWDER SPRAY

The preparation of a dry spray can be obtained from the following compounds:

| Anthralin-25-hydroxy cholesterol | 1.14 g |
|---|---|
| Colloidal silica | |
| Zinc oxide | 20 g |
| Talc | |
| Propellant gases trichlorofluoromethane dichlorofluoromethane | qsp 150 g |

We claim:

1. A complex based on anthralin and a sterol, characterized in that its melting point is 10° to 25° C. lower than that of the constituent of the complex melting at the lowest temperature and that the proportion of anthralin varies between 10 and 90 mol %.

2. A complex according to claim 1, characterized in that the sterol is selected from among:
   (i) cholesterol
   (ii) the derivatives that contain mono- and polyhydroxy or carboxy substituents on the $C_{17}$ side chain of cholesterol and the esters of said derivatives,
   (iii) the derivatives obtained by isomerization and/or creation of unsaturated bonds in the $C_{17}$ side chain of cholesterol, and
   (iv) the esters with up to 12 carbon atoms and the ethers having up to 6 carbon atoms in the $C_3$ position of cholesterol.

3. A complex according to claim 1 characterized in that it is selected from among the following:
   (i) anthralin (about 0.26 mol %) - cholesterol (about 0.7 mol %),
   (ii) anthralin (about 0.70 mol %) - 25-hydroxycholesterol (about 0.30 mol %),
   (iii) anthralin (about 0.30 mol %) - stigmasterol (about 0.70 mol %),
   (iv) anthralin (about 0.42.mol %) - cholesterol acetate (about 0.58 mol %),
   (v) anthralin (0.17 mol %) - 20-hydroxycholesterol (about 0.83 mol %), and
   (vi) anthralin (about 0.35 mol %) - methyl ester of (3-hydroxychol-5-en)-24-oic acid (about 0.65 mol %).

4. The complex according to claim 3, characterized in that it is the anthralin - cholesterol complex and it has a melting point of 132°±2° C.

5. The complex according to claim 3, characterized in that it is the anthralin - 25-hydroxycholesterol complex and it has a melting point of 157°±2° C.

6. The complex according to claim 3, characterized in that it is the anthralin - stigmasterol complex and it has a melting point of 150°±2° C.

7. The complex according to claim 3, characterized in that it is the anthralin - cholesterol acetate and it has a melting point of 102°±2° C.

8. The complex according to claim 3, characterized in that it is the anthralin - 20-hydroxycholesterol complex and it has a melting point of 118°±2° C.

9. The complex according to claim 3, characterized in that it is the anthralin - methyl ester of (3-hydroxychol-5-en)-24-oic acid complex and it has a melting point of 126°±2° C.

10. A process for preparation of a complexes according to claim 1, characterized in that it consists in heating, under agitation and under nitrogen, the mixture of anthralin and the sterol at a temperature close to that of the melting point of the compound that has the highest melting temperature, in maintaining that temperature for approximately 10 to 20 minutes and in isolating the complex in the form of a powder.

11. A pharmaceutical or cosmetic composition, characterized in that it contains a dermatologically effective amount of at least one anthralin/sterol complex of the type claimed according to any one of claims 1 to 9, in a pharmaceutically or cosmetically acceptable vehicle.

12. The composition according to claim 11, characterized in that the anthralin/sterol complex is present in a proportion of between 0.5 and 10% by weight.

13. The composition according to claim 11 characterized in that it is presented in the form of an ointment, a water-in-oil emulsion or a film, or in dry form.

14. The composition according to claim 13, characterized in that the water-in-oil emulsion contains, as thickening agent, an elastomeric silicone of the polyvinyl dimethylsiloxane type associated with a bulking agent of silica a thickening agent.

* * * * *